(12) United States Patent
Waldron et al.

(10) Patent No.: US 7,481,873 B2
(45) Date of Patent: *Jan. 27, 2009

(54) SMALL PARTICLE COPPER PYRITHIONE

(75) Inventors: Craig Waldron, Wolcott, CT (US);
Robert J. Martin, Monroe, CT (US);
Sonia R. Oberson, Shelton, CT (US);
Christopher J. Bannon, Manchester, CT (US)

(73) Assignee: Arch Chemicals, Inc., Norwalk, CT (US)

( * ) Notice: Subject to any disclaimer, the term of this patent is extended or adjusted under 35 U.S.C. 154(b) by 558 days.

This patent is subject to a terminal disclaimer.

(21) Appl. No.: 10/994,427

(22) Filed: Nov. 22, 2004

(65) Prior Publication Data

US 2005/0118134 A1     Jun. 2, 2005

Related U.S. Application Data

(63) Continuation-in-part of application No. 10/325,195, filed on Dec. 20, 2002, now Pat. No. 6,821,326.

(51) Int. Cl.
*A01N 31/00* (2006.01)
*A01N 33/24* (2006.01)
*A01N 43/72* (2006.01)

(52) U.S. Cl. .................. 106/18.33; 424/405; 514/186; 514/188; 514/937; 516/31; 516/77; 523/122

(58) Field of Classification Search .............. 106/18.33; 424/405; 514/186, 188, 937; 516/31, 77; 523/122

See application file for complete search history.

(56) References Cited

U.S. PATENT DOCUMENTS

| | | | |
|---|---|---|---|
| 4,323,683 A | 4/1982 | Bolich, Jr. et al. | |
| 4,345,080 A | 8/1982 | Bolich, Jr. | |
| 4,670,430 A | 6/1987 | Imamura et al. | |
| 5,057,153 A | 10/1991 | Ruggiero | |
| 5,185,033 A | 2/1993 | Hani et al. | |
| 5,238,490 A | 8/1993 | Farmer, Jr. et al. | |
| 5,246,489 A | 9/1993 | Farmer, Jr. et al. | |
| 5,319,000 A | 6/1994 | O'Connor et al. | |
| 5,540,860 A | 7/1996 | Hosseini et al. | |
| 5,650,095 A | 7/1997 | Hosseini et al. | |
| 5,723,112 A | 3/1998 | Bowser et al. | |
| 6,017,562 A | 1/2000 | Kaufman et al. | |
| 6,017,936 A | 1/2000 | Polson et al. | |
| 6,242,007 B1 | 6/2001 | Mohseni et al. | |
| 6,432,432 B1 | 8/2002 | Mohseni et al. | |
| 6,465,015 B1 | 10/2002 | Mohseni et al. | ............. 424/489 |
| 6,627,665 B2 | 9/2003 | Waldron et al. | |
| 6,821,326 B2 * | 11/2004 | Waldron et al. | .......... 106/18.33 |
| 2002/0197283 A1 | 12/2002 | Mohseni et al. | |
| 2003/0073749 A1 | 4/2003 | Waldron et al. | |

FOREIGN PATENT DOCUMENTS

| | | |
|---|---|---|
| EP | 1080640 | 7/2001 |
| WO | 00/54589 | 9/2000 |
| WO | 00/73272 | 12/2000 |
| WO | WO 2004/091875 | 10/2004 |

OTHER PUBLICATIONS

Article entitled "Sampling Criteria for Airborne Particulate Matter", found in the 2002 Threshold Limit Values and Biological Exposure Indices, pp. 73-76, no month.

* cited by examiner

*Primary Examiner*—Anthony J Green
(74) *Attorney, Agent, or Firm*—Dale L. Carlson; Wanli Wu; Wiggin and Dana LLP

(57) ABSTRACT

Disclosed herein is a composition comprising a non-dusting copper pyrithione dispersion comprising small solid particles of copper pyrithione dispersed in a liquid dispersant, said solid particles having a particle size within a range of from about 0.1 to about 10 microns and a median particle size of from 0.2 to less than 0.5 microns. The dispersion is suitably employed as an antifouling additive for marine paints without risking worker exposure to copper pyrithione dust. Paints containing the small particle copper pyrithione exhibit improved antifouling performance in cold water, as compared to paint containing larger particle copper pyrithione.

28 Claims, No Drawings

SMALL PARTICLE COPPER PYRITHIONE

CROSS REFERENCE TO RELATED APPLICATIONS

This application is a continuation-in-part application of U.S. Ser. No. 10/325,195, filed on Dec. 20, 2002, entitled "SMALL PARTICLE COPPER PYRITHIONE", now U.S. Pat. No. 6,821,326.

BACKGROUND OF THE INVENTION

1. Field of the Invention

The present invention relates generally to small particle copper pyrithione compositions, and a method of preparing these compositions. Preferably the compositions are provided in a non-dusting form as a dispersion of the small particles in an aqueous or organic solvent carrier. Alternatively, the small particles are provided in the form of a solid powder for use in facilities equipped to avoid or minimize human exposure to, and handling of, the powder. The small particle copper pyrithione compositions are suitable for use as antifouling agents in antifouling paints, such as marine paints. These small particles exhibit enhanced storage stability in dispersions with liquid media, as well as an enhanced leach rate from the antifouling paints, relative to larger size copper pyrithione particles.

2. Description of the Related Art

Pyrithione salts are well known compounds that are useful in a wide variety of applications including their use biocides, such as fungicides and bactericides. Heavy metal salts of pyrithione, including zinc, tin, cadmium and zirconium, as well as the magnesium and aluminum salts, have been produced in the form of flat platelets suitable for use in shampoo, are disclosed in U.S. Pat. Nos. 4,345,080 and 4,323,683.

Small particles of metal salts of pyrithione have been disclosed for use on the skin and hair. Illustratively, U.S. Pat. No. 4,670,430 discloses polyvalent metal salts of 2-mercaptopyridine-N-oxide in the form of a fine powder of particles in which at least fifty percent of the particles have a particle size below 0.2 micron. The '430 patent discloses that, when this fine particle of particles is incorporated into shampoo or rinse compositions, the dispersion stability of these salts is improved and the adsorbability of the particles onto the skin and hair is enhanced. Another illustration of the use of small particles of metal pyrithiones in hair treatment is provided in U.S. Pat. No. 5,723,112. The '112 patent discloses an antimicrobial hair treatment composition comprising (a) a surfactant, (b) fine particles of an insoluble particulate metal pyrithione in which at least 90% by weight of the particles have a size of five microns or less, and (c) a polymeric cationic deposition aid for the small particles.

Pyrithiones have also been used as antimicrobial additives in a variety of paints. Illustratively, various paints containing a pyrithione salt (e.g. zinc or sodium pyrithione) plus a copper salt (e.g. cuprous oxide or cuprous thiocyanate) are known in the art, as disclosed, for example, in U.S. Pat. No. 5,057,153. As another illustration, U.S. Pat. No. 5,185,033 describes a process for making a paint or paint base containing copper pyrithione or pyrithione disulfide plus cuprous oxide, wherein the paint exhibits stability against gelation during storage. As yet another illustration, U.S. Pat. No. 5,246,489 discloses a process for providing in situ generation of copper pyrithione in a paint or paint base which comprises incorporating a metal salt of pyrithione, cuprous oxide and a controlled amount of water into the paint either during or after the formation of the paint.

In many applications, copper pyrithione offers several advantages over other forms of pyrithione such as zinc pyrithione. For example, copper pyrithione is more stable than zinc pyrithione when added to paint products, and therefore is less likely to cause gelation during storage.

Commercially available copper pyrithione is typically sold as a dry powder. Generally, the particle size range for this commercial dry powder is between about 0.8 micron and about 30 microns, with a median particle size of from 3 to 6 microns. A key disadvantage of this commercial powder is that it generates dust during handling, necessitating special handling equipment, particularly since copper pyrithione powder was shown to be more toxic than zinc pyrithione powder when tested for acute inhalation toxicity in rats. This dusting issue associated with copper pyrithione dry powder is addressed in PCT publication WO00/54589. This publication discloses resolving the dusting issue using dispersions of solid copper pyrithione in a liquid dispersing medium.

The present inventors have now observed that, in use, although the dispersions of the PCT publication WO00/54589 obviate the dusting issue, they are subject to another problem. More specifically, paints made with these dispersions tend to provide a decreased leaching rate of copper pyrithione out of the paint in a low temperature environment. Such decreased leaching increases the likelihood that not enough antifouling agent will leach from the paint to prevent marine fouling at the paint's surface. The present invention provides one solution to this decreased leach rate problem, thereby insuring desired low temperature antifouling efficacy for copper pyrithione-containing antifouling paints.

SUMMARY OF THE INVENTION

In one aspect, the present invention relates to a composition comprising small particles of copper pyrithione having a particle size within a range of from about 0.1 to about 10 microns, and a median particle size of from 0.2 to less than 0.5 microns. These small particles exhibit enhanced antimicrobial performance, as compared to larger size copper pyrithione particles, in a marine paint that is exposed to a cold water environment of from about 5 degrees Centigrade to about 15 degrees Centigrade. In another aspect, the invention relates to a paint containing the small particles of copper pyrithione. In another aspect, the invention relates to a method for enhancing the antifouling efficacy of a paint in a cold water environment, said method comprising incorporating the small particles of pyrithione into the paint. These small particles of copper pyrithione exhibit a leach rate of at least one microgram per square centimeter per day based on exposure of the paint to cold water environment.

In another aspect, the present invention relates to a composition comprising a non-dusting copper pyrithione dispersion comprising small solid particles of copper pyrithione dispersed in a liquid dispersant. Preferably, the solid particles have a particle size within a range of from about 0.1 to about 10 microns, and a median particle size of from 0.2 to less than 0.5 microns. Optionally, the dispersion additionally contains a dust-inhibiting agent selected from the group consisting of surfactants, polymer resins, binders, and combinations thereof.

In another aspect, the present invention relates to a method of making a non-dusting dispersion of small solid particles of copper pyrithione dispersed in a liquid dispersant comprising the steps of:

(a) providing small solid particles of copper pyrithione within a desired size range of from about 0.1 to about 10 microns, and a median particle size of from 0.2 to less than 0.5 microns, by subjecting larger solid particles of copper pyrithione to a force selected from the group consisting of grinding, milling, pulverizing, sonicating, and combinations thereof, and (b) dispersing copper pyrithione particles in a liquid dispersant.

In yet another aspect, the present invention relates to a method of making a non-dusting dispersion of small solid particles of copper pyrithione dispersed in a liquid dispersant comprising the steps of:

(a) dispersing larger solid particles of copper pyrithione in a liquid dispersant to provide a liquid dispersion have said larger solid particles dispersed therein, and (b) subjecting said liquid dispersion of copper pyrithione to a force selected from the group consisting of grinding, milling, pulverizing, sonicating, and combinations thereof, in order to reduce the size of said larger size particles in said dispersion within a desired size range of from about 0.1 to about 10 microns, and a median particle size of from 0.2 to less than 0.5 microns.

In still another aspect, the present invention relates to a method of enhancing the antifouling characteristics of a paint which comprises adding to the paint an antifouling effective amount of solid particles of copper pyrithione having a particle size within a range of from about 0.1 to about 10 microns, and a median particle size of from 0.2 to less than 0.5 microns.

In yet another aspect, the present invention relates to a method of enhancing the antifouling characteristics of a paint which comprises adding to the paint an antifouling effective amount of a non-dusting copper pyrithione dispersion comprising small solid particles of copper pyrithione dispersed in a liquid dispersant, said solid particles having a particle size within a range of from about 0.1 to about 10 microns, and a median particle size of from 0.2 to less than 0.5 microns.

In still another aspect, the present invention relates to an antifouling paint comprising a paint base and an antifouling effective amount of solid particles of copper pyrithione having a particle size within a range of from about 0.1 to about 10 microns, and a median particle size of from 0.2 to less than 0.5 microns.

In yet another aspect, the present invention relates to an antifouling paint comprising a paint base and an antifouling effective amount of solid particles of copper pyrithione having a particle size within a range of from about 0.25 to about 7 microns, and a median particle size of from 0.2 to 0.49 microns.

In still another aspect, the present invention relates to a method of enhancing, in a cold water marine environment, the leach rate of copper pyrithione from a copper pyrithione-containing paint, said method comprising incorporating into the paint solid particles of copper pyrithione having a particle size within a range of from about 0.1 to about 10 microns and a median particle size of from 0.2 to less than 0.5 microns, in order to provide a copper pyrithione leach rate from the paint of at least one microgram per square centimeter per day of exposure of said paint to said cold water marine environment when measured at a cold water temperature of 10.6 degrees Centigrade.

In yet another aspect, the present invention relates to a copper pyrithione-containing antifouling paint providing an enhanced rate of leaching of the copper pyrithione from the paint in a cold water marine environment, said paint comprising a paint base and an antifouling effective amount of solid particles of the copper pyrithione, said solid particles having a particle size within a range of from about 0.1 to about 10 microns, and a median particle size of from 0.2 to less than 0.5 microns, said solid particles having a leach rate from the paint of at least one microgram per square centimeter per day of exposure of said paint to said cold water marine environment when measured at a cold water temperature of 10.6 degrees Centigrade.

These and other aspects of the present invention, will become apparent upon reading the following detailed description of the invention.

DETAILED DESCRIPTION OF THE INVENTION

It has now been surprisingly found by the present inventors that small particles of copper pyrithione exhibit an enhanced leach rate from antifouling paints containing these small particles, notably in a cold water environment. Without wanting to be bound by any particular theory, the present inventors hypothesize that small particles of copper pyrithione having a median size between 0.2 and less than 0.5 microns, exhibit a greatly enhanced leach rate from antifouling paints containing these small particles. This enhanced leach rate enhances the antifouling efficacy of the paint in that environment, as compared to paint containing larger size copper pyrithione particles.

As used herein, the term "cold water environment" denotes a water temperature of from about 5 degrees Centigrade to about 15 degrees Centigrade. As used herein the terms "small size" and "small solid", as used in reference to copper pyrithione particles, denotes those particles having a particle size within a range of from about 0.1 to about 10 microns, and a median particle size of less than 3.0 microns. Preferably the particle size is within a range of from about 0.25 to about 7 microns, with a median particle size of less than 2 microns. Preferably the median particle size is from 0.2 to less than 0.5 microns. Most preferably the median particle size is from 0.2 to 0.49 microns.

The invention also provides a non-dusting composition comprising the small particles of pyrithione dispersed in a liquid dispersant, optionally in the presence of one or more dust-inhibiting agents. This solid/liquid dispersion is easy to handle, and it reduces or eliminates the risk of inhalation exposure of airborne levels of copper pyrithione. Moreover, the small particles of copper pyrithione are physically stable in the dispersion, and in paint, during storage and prior to use. This minimizes the likelihood of the formation of copper pyrithione gels or thick thixotropic precipitates, thus providing an enhanced shelf life for the dispersions and paints, as compared to dispersions and paints containing larger sized particles of copper pyrithione.

As used herein, the term "dispersion" is intended to encompass both low viscosity solid/liquid mixtures, and higher viscosity solid/liquid compositions, such as pastes. Generally, the dispersion has a viscosity in the range of from about 1,000 cps to about 100,000 cps at room temperature, preferably between about 5,000 cps and 70,000 cps at room temperature, wherein "cps" denotes Centipoise. Advantageously, the dispersion comprises from about 20% to about 99.95% (preferably from about 20% to about 70%) by weight of small particles of solid copper pyrithione particles dispersed in from about 0.05% to about 80% (preferably from about 30% to about 80%) by weight of a liquid dispersant selected from the group consisting of water, organic solvents, and combinations thereof. Optionally, the dispersion additionally contains from about 0.05% to about 30% of a dust-inhibiting agent selected from the group consisting of surfactants, polymer resins, binders, and combinations thereof. All of these weight percents are based on the total weight of the dispersion.

As used herein, the terms "non-dusting" and "dust-free" refer to a composition that is substantially free of, advantageously greater than least 99% by weight free of, airborne copper pyrithione particles. The term "dust-inhibiting agent" refers to compounds that assist in preventing or inhibiting the formation of dust in the form of airborne copper pyrithione particles, as compared to a composition that does not contain those compounds. "Airborne particles" are described in detail in an article entitled "Sampling Criteria for Airborne Particulate Matter" found in the "1999 Threshold Limit Values and Biological Exposure Indices" published by the American Conference of Governmental Industrial Hygienists. That publication states that, for chemical substances present in inhaled air as suspensions of solid particles or droplets, the potential hazard associated with airborne particles is a function of particle size the relevant particles as well as the mass concentration of particles.

As noted above, the present invention relates to a composition comprising a non-dusting copper pyrithione dispersion of small solid particles of copper pyrithione dispersed in a liquid dispersant selected from the group consisting of water, organic solvents, and combinations thereof. Optionally, the dispersion additionally contains a dust-inhibiting compound selected from the group consisting of surfactants, polymer resins, binders, and combinations thereof. Each of these components is described in more detail herein.

Copper pyrithione is available commercially (from Arch Chemicals, Inc., Norwalk, Conn.) in the form of a dry powder. This form of copper pyrithione may be employed as starting material in the method of the present invention.

Alternatively, copper pyrithione may be made by conventional methods known in the art, as disclosed in U.S. Pat. Nos. 5,650,095; 5,540,860; 5,238,490, all of which are incorporated by reference herein. Briefly, copper pyrithione may be made by reacting a copper salt and/or copper oxide with a pyrithione salt in an aqueous or organic carrier medium. Suitable pyrithione salts are those which are soluble in the organic or aqueous carrier, such as sodium, calcium, potassium, and magnesium salts of pyrithione, pyrithione acid or the non-metal salts such as the ethanolamine salt, chitosan salt, and the disulfide salt of pyrithione (which is commercially available from Arch Chemicals, Inc. as "OMADINE MDS"). The pyrithione salt is preferably employed in an amount of between about 1 and about 40 weight percent, more preferably between 5 and 25, and most preferably between about 15 and 25 weight percent, all weight percents being based on the total weight of the reaction mixture, in order to prepare the desired copper pyrithione.

The copper salt used to prepare copper pyrithione is suitably any salt containing copper that is soluble in the carrier employed in the reaction. For example, if water is the carrier, useful copper salts include copper chloride dihydrate, copper sulfate, copper carbonate, copper nitrate, copper acetate, as well as combinations thereof. The above copper salts may be used individually or in combination, or in combination with copper oxide.

The copper salt, copper oxide and/or copper salt/copper oxide combination, used to prepare copper pyrithione, is preferably employed in an amount of between about one and about 50 weight percent, more preferably between 5 and 30 weight percent, and most preferably between about 15 and 20 weight percent, based on the total weight of the reaction mixture.

Carriers that are useful in the reaction mixture for preparing the copper pyrithione include water, organic solvents, and combinations thereof. Useful organic solvents include alcohols such as methanol and ethanol, amines such as diethanolamine, ethers, esters, and the like.

The non-dusting small particle size copper pyrithione composition is produced by combining the copper pyrithione, prepared as described above, with an aqueous or organic dispersant, and optionally incorporating a dust-inhibiting agent. The reduction of the particle size of the copper pyrithione component can occur either prior to, simultaneously with, or after, making the copper pyrithione dispersion. Illustratively, the small particle size-copper pyrithione can be made either during the manufacturing precipitation of copper pyrithione, prior to the making of the dispersion by milling the dry powder to the desire size, or during the preparation of the dispersion using a device that generates pulverizing forces, such as a mill, to decrease the particle size of the copper pyrithione particles. As another alternative, the particle size of the copper pyrithione particles can be reduced after performing the dispersing step by subjecting the dispersion to pulverizing forces, such as by running it through a particle size reducing mill. Suitable particle size reducing mills include Jet, Air classifying (ACM)), Netzsch, ball, or combination of such mills. As another alternative, equipment that produces pulverizing forces by means of ultrasound, such as sonication devices, may be used to provide pulverizing forces.

If sonication is used, the sonic energy employed preferably has a frequency of from about 20 Hz to about 250,000 Hz (250 kHz), more preferably from about 5 kHz to about 105 kHz, and most preferably from about 16 kHz to about 20 kHz. Combinations of frequencies may also be used, depending on the configuration of the particular sonication apparatus. The energy level output that results from the sonic energy applied to the reaction mixture is preferably in the range from about 20 to about 5000 Watts, more preferably from about 100 to about 1000 Watts, and most preferably from about 400 to about 600 Watts. An example of a suitable sonication device suitable for use in the method of the invention is a Nearfield NAP Model 3606 acoustical processor (available commercially from Advanced Sonic Processing Systems, Woodbury, Conn.), although any sonication device may be employed in the method of the invention.

The copper pyrithione is preferably employed in the dispersion in an amount of between about 20 and 95 weight percent, more preferably between about 30 and 70 weight percent, even more preferably between about 30 and 50 weight percent, and most preferably between about 35 and about 60 weight percent. All weight percents are based upon the total weight of the dispersion. A particularly useful amount of copper pyrithione is about 45 weight percent.

The optional dust-inhibiting component of the composition of the present invention is preferably one or more surfactants, one or more polymer resins, one or more binders, or combinations thereof. If used, this component generally comprises from about 0.05 to about 30 weight percent of the composition of the invention. If used, the dust inhibiting agent is preferably employed in a total amount of between about 0.05 and about 10% by weight, more preferably between 0.1 and about 5% by weight, and most preferably between about 0.5 and about 2% by weight, all weight percents being based upon the total weight of the dispersion.

Suitable resins for use as the dust-inhibiting component in the dispersion of the present invention include acrylic resins, vinyl resins, alkyd resins, epoxy resins, polyurethane resins, natural resins, rosins, polyester resins, plastisols, and combinations thereof. Vinyl resin is particularly useful in the composition of the present invention.

Plastisols suitable for use as the dust inhibiting component in the dispersion of the present invention comprise a resin plus a carrier, such as a plasticizer, as described in U.S. Pat. No. 5,319,000, herein incorporated by reference in its entirety, including commercially available plastisols containing plasticizers and resin-compatible additives. Preferable amounts of the resin component of the plastisol generally range from between about 0.2% by weight and about 30% by weight, based upon the total weight of the plastisol.

Binders suitable for use as the dust inhibiting component in the dispersion of the present invention include any low-melt polymer or wax known in the binding arts. Exemplary binders include rosins such as rosins sold under the trade name "TACOLYN" or "PICOTEX" (hydrocarbon resin monomer produced from co-polymerization of vinyl toluene and alpha-methystyrene), acrylates such as methyl acrylate, ethyl acrylate, and the like, xanthate or guar gums, polyvinyl alcohol, ethyl acetate, and combinations thereof. Useful amounts of the binder component preferably range from about 0.1 to about 20 weight percent, more preferably from about 0.5 to about 10 weight percent, and most preferably from about 0.5 to about 5 weight percent, all weight percents being based on the total weight of the composition.

As indicated above, the optional dust-inhibiting agent component of the composition of the present invention may be used individually (e.g., only a surfactant, or only a polymer resin as the dust-inhibiting component). Alternatively, combinations of one or more of the above-described dust inhibiting agents may be used as the dust-inhibiting component. Moreover, it is possible to employ one or more of the above-described dust-inhibiting agents (e.g., surfactants) in combination with one or more other dust-inhibiting agents (e.g., polymer resins) to produce the dust-inhibiting component of the present invention.

As indicated above, the copper pyrithione in the dispersion of the present invention may take the form of a small particle powder, (e.g., a dispersion), or, alternatively, larger non-inhalable granules made up of small particles (e.g., granules greater than 4 microns (4 microns and larger) Generally, the particle size range for the copper pyrithione powder commercially available is between about 0.80 micron and about 30 microns, with a median particle size between 3 to 6 microns.

In a particularly advantageous dispersion of the present invention, the dust-inhibiting agent is preferably one or more surfactants and/or one or more polymer resins and/or one or more binders, and the non-dusting small particle copper pyrithione dispersion is prepared generally as follows:

The selected polymer resin and/or surfactant is first added to a mixing vessel and dissolved in the solvent of choice with low speed mixing (generally from about 500-800 rpm) using a high speed disperser type of mixer well known in the paint and coating art. The copper pyrithione powder is next added, and the mixing speed is increased to between 1,000-3,000 rpm. Mixing is continued until a homogenous dispersion or paste is produced, generally from about 1 minute to about 30 minutes. Than this dispersion is added to a grinding mill such as a Netzsch Zeta Mill and mixed from 10 minutes to 8 hours or until the desired small particle size is achieved.

Another method for preparing the small particle copper pyrithione dispersion would be to dry and mill the powder down to a small particle size first using a jet mill or a air classifying mill that can achieve the desired small particles first. Then this small particle powder is added to the selected polymer resin and/or surfactant in a mixing vessel with the solvent of choice and mixed using a high-speed disperser type of mixer well known in the paint and coating art. The mixing speed is between 1,000-5,000 rpm. Mixing is continued until a homogenous dispersion or paste is produced, generally from about 5 minute to about 50 minutes.

If copper pyrithione wet filter cake is used to make an organic solvent based dispersion, remaining water must be removed from the final composition. In one embodiment, the above mixing step is done in a closed flask or reactor with a Dean-Stark trap connection or another device used for removing the water from the organic solvent. The mixture may be heated to between about 95° C. to 105° C. or higher until no more water is being removed from the dispersion. Alternatively, the mixing can be done under vacuum with lower (or no) required heating temperatures. Than this dispersion is added to a grinding mill if needed such as a Netzsch Zeta Mill for reduction of particle size and mixed from 15 minutes to 5 hours or until the desired small particle size is achieved.

The non-dusting small particle copper pyrithione composition of the present invention may be made as a dispersion, which takes the form of a thick paste. When made with water as the dispersant, the composition of the invention has a viscosity generally in the range of from about 1,000 centipoise (cps) to about 75,000 cps at room temperature. The non-dusting small particle copper pyrithione composition of the present invention made with an organic solvent has a viscosity generally in the range of from about 5,000 cps to about 100,000 cps (preferably 5,000 to about 70,000 cps) at room temperature.

The non-dusting small particle copper pyrithione composition of the present invention offers significant advantages over the copper pyrithione compositions of the prior art. The non-dusting small particle copper pyrithione compositions of the present invention provide easy processing and mixing with paints, coatings, or personal care compositions, such as soaps, shampoos, medicaments, and the like. The dust-inhibiting properties of the present invention significantly reduce the presence of airborne copper pyrithione dust in the local environment. As a result, the non-dusting small particle copper pyrithione compositions of the present invention can be handled easily with reduced risk without fear of inhalation of toxic airborne copper pyrithione powder. In addition, it has been found that when the small particle copper pyrithione dispersion is spilled and the solvent evaporates, the dust-inhibiting component in the dispersion forms a film on the copper pyrithione, which minimizes dusting. Further, the small particles of copper pyrithione seem to stay suspended better in dispersions so no thick thixotropic precipitates, and therefore increases the shelf life of the present composition.

When added to marine paints this present invention offers significant advantages over the copper pyrithione compositions of the prior art. The non-dusting small particle copper pyrithione compositions of the present invention when mixed into a paint, the resulting film coating produced from this paint leaches a higher amount of copper pyrithione at the surface of the coating. This is an advantage because copper pyrithione has a water solubility of less than 0.50 ppm. In certain marine antifouling paint films if the copper pyrithione does not leach out at a high enough concentration marine fouling organisms will settle on the surface of the film.

Preferably, the small particles of copper pyrithione are present in an anti-fouling paint in an amount of from about 0.5% to about 10% by weight based on the total weight of the anti-fouling paint. More preferably the small particles of copper pyrithione are present in an anti-fouling paint in an amount of from about 0.5% to about 5% by weight, based on the total weight of the anti-fouling paint.

Data from the ASTM lab method used to determine the leach rates of biocides form marine paint film show that copper pyrithione leach rate is dependent on temperature. The higher the temperature of the water the higher the leach rate. Upon doing these leach rate test much to the surprise of the authors the copper pyrithione leach rate was also dependant on the particle size of the copper pyrithione added to the paint. The smaller the particle size of copper pyrithione the higher the leach rate of copper pyrithione from the film at all temperatures tested.

EXAMPLES

The invention is further described by the following Examples, but is not intended to be limited by these Examples. All parts and percentages are by weight and all temperatures are in degrees Celsius unless explicitly stated otherwise. All weight percents are based on the total weight of each composition, unless explicitly stated otherwise.

Comparative Example A

Preparation of a Copper Pyrithione (CuPT) Dispersion in Xylene

As a comparison to the dispersions of the present invention, 1300 grams "LAROFLEX MP25" polymer resin (vinyl chloride-isobutyl vinyl ether copolymer, a product of BASF Corporation, Charlotte, N.C.) was dissolved into 8.32 kilograms of xylene. Following dissolution of the polymer, 8.62 kilograms of copper pyrithione (A product of Arch Chemicals ACBV Swords, Ireland) (49% by weight) was added slowly and with constant mixing using a high speed disperser at a speed of 1000-2000 rpms. The mixture was stirred at low speed (1000 rpm) and with low shear for 0.5 hours to provide adequate mixing until a homogenous mixture was achieved. The copper pyrithione powder used to make this dispersion was analyzed on a Horiba Laser light scattering particle size analyzer before, and after, it was added to the dispersion and the below data was obtained.

TABLE 1

Median Particle Size Using Commercially Available Copper Pyrithione

| Copper Pyrithione Arch Chemicals | Median Particle Size (Microns) | Mean Particle Size (Microns) |
| --- | --- | --- |
| Before Mixing | 3.35 | 3.01 |
| After Mixing | 3.30 | 3.00 |

As observed from the data in the above table the low shear mixing of the copper pyrithione powder in the dispersion did not change the particle size of the copper pyrithione.

Example 1

Preparation of a Very Small Particle Size Copper Pyrithione Dispersion in Xylene A 8.0 kilogram size sample was taken from the dispersion of Example A, and the sample was diluted down to a concentration of 45.0% copper pyrithione by adding xylene solvent. The diluted sample was then run though a LMZ 2 Model Netzsch mill for 2 hours at ~2000 rpm. The resulting copper pyrithione dispersion was analyzed on a Horiba Laser light scattering particle size analyzer and the below data was obtained.

TABLE 2

Median Particle Size Before and After Netzsch Milling A Copper Pyrithione Dispersion in Xylene

| Copper Pyrithione Dispersion Arch Chemicals | Median Particle Size (Microns) | Mean Particle Size (Microns) |
| --- | --- | --- |
| Before Netzsch Milling | 3.30 | 3.00 |
| After Netzsch Milling | 0.40 | 0.41 |

The Netzsch milled dispersion exhibited much better shelf life stability than the dispersion made in Example A.

Example 2

Preparation of a Very Small Particle Size Copper Pyrithione Dispersion in Xylene A 8.0 kilogram size sample was taken from the dispersion of Example A, and the sample was diluted down to a concentration of 40.0% copper pyrithione by adding xylene solvent. The diluted sample was then run though a LMZ 2 model Netzsch mill for 3 hours at ~2000 rpm. The resulting copper pyrithione dispersion was analyzed on a Horiba Laser light scattering particle size analyzer and the below data was obtained.

TABLE 3

Median Particle Size Before and After Netzsch Milling A Copper Pyrithione Dispersion in Xylene

| Copper Pyrithione Dispersion Arch Chemicals | Median Particle Size (Microns) | Mean Particle Size (Microns) |
| --- | --- | --- |
| Before Netzsch Milling | 3.30 | 3.00 |
| After Netzsch Milling | 0.33 | 0.38 |

The Netzsch milled dispersion exhibited much better shelf life stability than the dispersion made in Example A.

Example 3 (Proposed)

Marine antifouling (AF) paints containing small copper pyrithione particles of Example 1 and 2 are tested for antifouling efficacy using the following protocol:

Five marine AF paints containing the below ingredients:

| Paint Number | Cuprous Oxide (Wt. %) | Copper Pyrithione (%) | Acrylic Polymer (%) |
| --- | --- | --- | --- |
| 1 | 40 | 0 | 15 |
| 2 | 40 | 3.0 | 15 |
| 3 | 40 | 3.0 | 15 |
| 4 | 40 | 3.0 | 15 |
| 5 | 40 | 3.0 | 15 |

The above paints are made on a high speed disperser with low shear mixing at 2000 rpm for 30 minutes.

The particle size of copper pyrithione in each paint is described in the below table.

| Paint Number | Copper Pyrithione Used | Median Particle Size (Microns) | Mean Particle Size (Microns) |
|---|---|---|---|
| 1 | None | — | — |
| 2 | Powder | 3.40 | 3.09 |
| 3 | Example A Dispersion | 3.36 | 3.05 |
| 4 | Example 1 Dispersion | 0.4 | 0.41 |
| 5 | Example 2 Dispersion | 0.33 | 0.38 |

A sample of each of five paints is painted onto fiberglass panels having dimensions of 6 inches by 16 inches. The five coated panels are submerged in ocean water off the coast of Maine (Portland) for a period of 5 months in order to provide a basis for comparing the antifouling efficacy of the paints in a cold water environment. The ocean water temperature varies from 6 degrees C. to 17 degrees C. during the period of the test, with the average water temperature being 11 degrees C.

After the test period, the five-coated panels are removed from the ocean water, and visually examined for barnacle and microorganism growth. The results of this examination provide the following comparative table.

Five-month exposure Data:

| Paint Number | Cuprous Oxide (Wt. %) | Copper Pyrithione (%) | Total Fouling on panel (%) |
|---|---|---|---|
| 1 | 40 | 0 | 35 |
| 2 | 40 | 3.0 | 25 |
| 3 | 40 | 3.0 | 25 |
| 4 | 40 | 3.0 | 4 |
| 5 | 40 | 3.0 | 3 |

While the invention has been described in combination with embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims. All patent applications, patents, and other publications cited herein are incorporated by reference in their entireties.

The invention claimed is:

1. A composition comprising small particles of copper pyrithione having a particle size within a range of from about 0.1 to about 10 microns, and a median particle size of from 0.2 to less than 0.5 microns, said small particles exhibiting enhanced antimicrobial performance, as compared to larger size copper pyrithione particles, in a marine paint that is exposed to a cold water environment of from about 5 degrees Centigrade to about 15 degrees Centigrade.

2. The composition of claim 1 wherein said small particles of copper pyrithione exhibit a leach rate of at least one microgram per square centimeter per day based on exposure of said paint to said cold water environment.

3. A paint containing the composition of claim 1 in an antifouling effective amount of from about one percent to about 5 percent based upon the total weight of the paint.

4. A method for enhancing the antifouling efficacy of a paint in a cold water environment, said method comprising incorporating the composition of claim 1 into the paint.

5. A composition comprising a non-dusting copper pyrithione dispersion comprising small solid particles of copper pyrithione dispersed in a liquid dispersant, said solid particles having a particle size within a range of from about 0.1 to about 10 microns and a median particle size of from 0.2 to less than 0.5 microns.

6. The composition of claim 5 wherein said solid particles have a particle size within a range of from about 0.25 to about 7 microns and a median particle size of from 0.2 to 0.49 microns.

7. The composition of claim 6 wherein said solid particles have a median particle size within a range of from about 0.2 to about 0.4 microns.

8. The composition of claim 7 wherein said solid particles have a median particle size within a range of from 0.3 to 0.4 microns.

9. The composition of claim 5 wherein said liquid dispersant is selected from the group consisting of water, organic solvents, and combinations thereof.

10. The composition of claim 5 wherein said solid particles are present in an amount of from about 20% to about 99.95% by weight and said liquid dispersant is present in an amount of from about 0.05% to about 80% by weight, based upon the total weight of the composition.

11. The composition of claim 5 wherein said solid particles are present in an amount of from about 20% to about 70% by weight, and said liquid dispersant is present in an amount of from about 30% to about 80% by weight based upon the total weight of the composition.

12. The composition of claim 5 wherein the composition additionally contains from about 0.05% to about 30%, based upon the total weight of the dispersion, of a dust-inhibiting agent selected from the group consisting of surfactants, polymer resins, binders, and combinations thereof.

13. A method of making a non-dusting dispersion of small solid particles of copper pyrithione dispersed in a liquid dispersant comprising the steps of:
    (a) providing small solid particles of copper pyrithione within a size range of from about 0.1 to about 10 microns, and a median particle size of from 0.2 to less than 0.5 microns, by subjecting larger solid particles of copper pyrithione to a force selected from the group consisting of grinding, milling, pulverizing, sonicating, and combinations thereof, and
    (b) dispersing said small copper pyrithione particles in a liquid dispersant.

14. The method of claim 13 wherein said milling is effected by a technique selected from the group consisting of ball milling, jet milling, air classifying milling (ACM), Netzsch milling, and combinations thereof.

15. A method of making a non-dusting dispersion of small solid particles of copper pyrithione dispersed in a liquid dispersant comprising the steps of:
    (a) dispersing larger solid particles of copper pyrithione in a liquid dispersant to provide a liquid dispersion have said larger solid particles dispersed therein, and
    (b) subjecting said liquid dispersion of copper pyrithione to a force selected from the group consisting of grinding, milling, pulverizing, sonicating, and combinations thereof, in order to reduce the size of said larger size particles in said dispersion within a size range of from about 0.1 to about 10 microns, and a median particle size of from 0.2 to less than 0.5 microns.

16. The method of claim 15 wherein said milling is effected by a technique selected from the group consisting of ball milling, jet milling, air classifying milling (ACM), Netzsch milling, and combinations thereof.

17. A method of enhancing the antifouling characteristics of a paint which comprises adding to the paint an antifouling effective amount of solid particles of copper pyrithione having a particle size within a range of from about 0.1 to about 10 microns and a median particle size of from 0.2 to less than 0.5 microns.

18. The method of claim 17 wherein the solid particles of copper pyrithione have a particle size within a range of from about 0.25 to about 7 microns and a median particle size of from 0.2 to 0.49 microns.

19. A method of enhancing the antifouling characteristics of a paint which comprises adding to the paint an antifouling effective amount of a non-dusting copper pyrithione dispersion comprising small solid particles copper pyrithione dispersed in a liquid dispersant, said solid particles having a particle size within a range of from about 0.1 to about 10 microns and a median particle size of from 0.2 to less than 0.5 microns.

20. An antifouling paint comprising a paint base and an antifouling effective amount solid particles of copper pyrithione having a particle size within a range of from about 0.1 to about 10 microns and a median particle size of from 0.2 to less than 0.5 microns.

21. The antifouling paint of claim 20 wherein said solid particles of copper pyrithione have a particle size within a range of from about 0.25 to about 7 microns and a median particle size of from 0.2 to 0.49 microns.

22. A method of enhancing, in a cold water marine environment, the leach rate of copper pyrithione from a copper pyrithione-containing paint, said method comprising incorporating into the paint solid particles of copper pyrithione having a particle size within a range of from about 0.1 to about 10 microns and a median particle size of from 0.2 to less than 0.5 microns, in order to provide a copper pyrithione leach rate from the paint of at least one microgram per square centimeter per day of exposure of said paint to said cold water marine environment when measured at a cold water temperature of 10.6 degrees Centigrade.

23. The method of claim 22 wherein said copper pyrithione is present in an antifouling effective amount of a non-dusting copper pyrithione dispersion comprising small solid particles of copper pyrithione dispersed in a liquid dispersant, said small solid particles having a particle size within a range of from about 0.1 to about 10 microns and a median particle size of from 0.2 to 0.49 microns.

24. The method of claim 22 wherein the composition additionally contains from about 0.05% to about 30%, based upon the total weight of the dispersion, of a dust-inhibiting inhibiting agent selected from the group consisting of surfactants, polymer resins, binders and combinations thereof.

25. A copper pyrithione-containing antifouling paint providing an enhanced rate of leaching of the copper pyrithione from the paint in a cold water marine environment, said paint comprising a paint base and an antifouling effective amount of solid particles of the copper pyrithione, said solid particles having a particle size within a range of from about 0.1 to about 10 microns, and a median particle size of from 0.2 to less than 0.5 microns, said solid particles having a leach rate from the paint of at least one microgram per square centimeter per day: of exposure of said paint to said cold water marine environment when measured at a cold water temperature of 10.6 degrees Centigrade.

26. The copper pyritbione-containing antifouling paint of claim 25 wherein said copper pyrithione is present in an antifouling effective amount of a non-dusting copper pyrithione dispersion comprising small solid particles of copper pyrithione dispersed in a liquid dispersant, said solid particles having a particle size within a range of from about 0.1 to about 10 microns and a median particle size of from 0.2 to less than 0.5 microns.

27. The copper pyrithione-containing antifouling paint of claim 25 wherein said dispersion additionally contains from about 0.05% to about 30%, based upon the total weight of the dispersion, of a dust-inhibiting agent selected from the group consisting of surfactants, polymer resins, binders, and combinations thereof.

28. The copper pyrithione-containing antifouling paint of claim 25, wherein said solid particles of copper pyrithione are present in an amount of from about 0.5% to about 5.0% by weight, based upon the total weight of the copper pyrithione-containing antifouling paint.

\* \* \* \* \*